(12) United States Patent
Nakajima et al.

(10) Patent No.: US 11,802,104 B2
(45) Date of Patent: Oct. 31, 2023

(54) METHOD FOR PREPARATION OF ACETOACETYLATED POLYOLS

(71) Applicant: ARXADA AG, Visp (CH)

(72) Inventors: Masaki Nakajima, Basel (CH); Anja Bierstedt, Visp (CH); Leo Schmid, Ried-Brig (CH); Maximilian Kuehnle, Rheinfelden (CH); Ulrich Mayerhoeffer, Visp (CH); Ellen Klegraf, Naters (CH)

(73) Assignee: ARXADA AG, Visp (CH)

( * ) Notice: Subject to any disclaimer, the term of this patent is extended or adjusted under 35 U.S.C. 154(b) by 0 days.

(21) Appl. No.: 17/599,614

(22) PCT Filed: Apr. 3, 2020

(86) PCT No.: PCT/EP2020/059629
§ 371 (c)(1),
(2) Date: Sep. 29, 2021

(87) PCT Pub. No.: WO2020/201534
PCT Pub. Date: Oct. 8, 2020

(65) Prior Publication Data
US 2022/0185762 A1 Jun. 16, 2022

Related U.S. Application Data

(60) Provisional application No. 62/829,145, filed on Apr. 4, 2019.

(30) Foreign Application Priority Data

Apr. 3, 2019 (EP) .................................. 19166933

(51) Int. Cl.
*C07C 67/46* (2006.01)
*C07C 69/72* (2006.01)

(52) U.S. Cl.
CPC .............. *C07C 67/46* (2013.01); *C07C 69/72* (2013.01)

(58) Field of Classification Search
CPC .......... C07C 67/46; C07C 69/72; C07C 69/38
See application file for complete search history.

(56) References Cited

U.S. PATENT DOCUMENTS

| 2,167,168 A * | 7/1939 | Boese, Jr. ............... C07C 69/72 |
| | | 560/178 |
| 2,351,366 A * | 6/1944 | Pohl ....................... C07C 327/00 |
| | | 560/178 |
| 3,117,156 A * | 1/1964 | Keller ..................... C07C 67/46 |
| | | 560/178 |
| 3,513,189 A * | 5/1970 | Marcus ................... C07C 67/46 |
| | | 560/138 |
| 5,459,178 A | 10/1995 | Chan et al. |

FOREIGN PATENT DOCUMENTS

| GB | 1131374 | 10/1968 |
| WO | WO0138289 | 5/2001 |

OTHER PUBLICATIONS

International Search Report and Written Opinion for PCT/EP2020/059629 dated Jun. 24, 2020, 12 pages.

* cited by examiner

*Primary Examiner* — Yate' K Cutliff
(74) *Attorney, Agent, or Firm* — Dority & Manning, P.A.

(57) ABSTRACT

The invention discloses a method for preparation of an acetoacetylated polyol by reaction of a polyol with deketene in the presence of a base and in the absence of a solvent.

9 Claims, No Drawings

METHOD FOR PREPARATION OF ACETOACETYLATED POLYOLS

CROSS REFERENCE TO RELATED APPLICATIONS

This application is the U.S. National Stage entry of International Application Number PCT/EP2020/059629 filed under the Patent Cooperation Treaty having a filing date of Apr. 3, 2020, which claims priority to U.S. Provisional Patent Application No. 62/829,145 having a filing date of Apr. 4, 2019, and European Patent Application No. 19166933.2 having a filing date of Apr. 3, 2019 which are incorporated herein by reference.

The invention discloses a method for preparation of an acetoacetylated polyol by reaction of a polyol with deketene in the presence of a base and in the absence of a solvent.

BACKGROUND OF THE INVENTION

U.S. Pat. No. 5,459,178 discloses the use of acetoacetylated polyols for the preparation of foundry mixes and their use to prepare foundry shapes made from foundry mixes by a no-bake process. The acetoacetylated polyols are prepared by a transesterification of a polyhydroxyl compound with an alkyl, preferably ethyl or t-butyl, acetoacetate in the presence of triphenyl phosphite, whereby the alcohol of the alkyl acetoacetate is liberated and needs to be separated from the reaction mixture.

There was a need for a method for preparation of acetoacetylated polyols, which has high yields and which does not need the presence of triphenyl phosphite, that does not need a transesterification process in order to avoid the need of separating the liberated alcohol from the reaction mixture.

The need was met by instant invention.

Abbreviations

DABCO 1,4-Diazabicyclo[2.2.2]octane, CAS 280-57-9
DMAP N,N-Dimethylpyridin-4-amin, CAS 1122-58-3
eq equiv., equivalent

SUMMARY OF THE INVENTION

Subject of the invention is a method for preparation of an acetoacetylated polyol, the method comprises a reaction REAC1, wherein a polyol is reacted with diketene;
REAC1 is done in the presence of a base BAS1;
BAS1 is DABCO or DMAP;
REAC1 is done in the absence of a solvent.

DETAILED DESCRIPTION OF THE INVENTION

The acetoacetylated polyol can also be called an acetoacetate ester of a polyol.

REAC1 is done neat, that is no solvent is charged to REAC1, no solvent is present in REAC1.

Preferably, only the three components polyol, BAS1 and diketene are used for and are charged for REAC1, and no other compounds are used for or are charged for or are present in REAC1.

Preferably, the polyol is a compound of formula (I);

$$R1(OH)_{m1} \quad (I)$$

R1 is selected from the group consisting of $C_{1-12}$ alkane, $C_{1-12}$ alkene, $C_{1-12}$ alkyne, $C_{5-12}$ cycloalkane, $C_{6-12}$ cycloalkene, $C_{8-12}$ di- and tricycloalkane, $C_{8-12}$ di- and tricycloalkene, and mixtures thereof;
wherein 1, 2 or 3 of any of the $CH_2$ group can be exchanged for O;
m1 is 2, 3, 4, 5 or 6.

More preferably, m1 is 2, 3, 4 or 6, so the polyol is a di-, tri, tetra or hexaol.

More preferably, 1, 2 or 3 of any of the endocyclic $CH_2$ groups can be exchanged for O; even more preferably, 1 or 2 of any of the endocyclic $CH_2$ groups can be exchanged for O.

More preferably, R1 is selected from the group consisting of $C_{1-12}$ alkane, $C_{1-12}$ alkene, $C_{1-12}$ alkyne, $C_{5-12}$ cycloalkane, $C_{8-12}$ di- and tricycloalkane, and mixtures thereof.

In one embodiment, the polyol is selected from the group consisting of di- and trimethylene glycol, ethylene glycol, di-, tri- and tetraethylene glycol, 1,2- and 1,3-propanediol, di- and tripropylene glycol, 1,2-, 1,3-, 1,4-, 2,3-, 2,4- and 3,4-butanediol, pentanediol, pentylglycol, neopentyl glycol, glycerol, isosorbide, hexanediol, hexylene glycol, trimethylpentanediol, tricyclo[5.2.1.0$^{2,6}$]decane-4,8-dimethanol, 1,2-, 1,3- and 1,4-cyclohexanedimethanol, 2,4-butyne-1,4-diol, 2,5-dimethyl-3-hexyne-2,5-diol, trimethylolethane, trimethylolpropane, sorbitol, pentaerythritol, and mixtures thereof.

In another embodiment, the polyol is selected from the group consisting of ethylene glycol, 1,2-propanediol, 2,3-butanediol, 1,4-butanediol, 1,5-pentanediol, glycerol, isosorbide, 1,6-hexanediol, tricyclo[5.2.1.0$^{2,6}$]decane-4,8-dimethanol, 1,4-cyclohexanedimethanol, 2,4-butyne-1,4-diol, 2,5-dimethyl-3-hexyne-2,5-diol, trimethylolpropane, sorbitol, pentaerythritol, and mixtures thereof.

In one embodiment the polyol is liquid at ambient temperature, in another embodiment the polyol is solid at ambient temperature.

In a preferred embodiment, the polyol is selected from the group consisting of ethylene glycol, 1,4-butanediol, 1,5-pentanediol, 1,6-hexanediol, tricyclo[5.2.1.0$^{2,6}$]decane-4,8-dimethanol, 1,4-cyclohexanedimethanol and trimethylolpropane, or mixtures thereof.

In an especially preferred embodiment, the polyol is selected from ethylene glycol and trimethylolpropane, or a mixture thereof.

Preferably, the acetoacetylated polyol is a compound of formula (II);

$$R1(O-CO-CH_2-CO-CH_3)_{m1} \quad (II)$$

with R1, m1 and the polyol as defined herein, also with all their embodiments.

Preferably, BAS1 is DABCO.

Preferably, the molar amount of BAS1 in REAC1 is from 0.0001 to 0.01 eq, more preferably from 0.0005 to 0.005 eq, even more preferably from 0.00075 to 0.0025 eq, of the molar amount of compound of formula (I).

Preferably, the molar amount of diketene in REAC1 is from 1 to 1.3 eq, more preferably from 1 to 1.2 eq, even more preferably from 1 to 1.1 eq, especially from 1 to 1.05 eq, of the total molar equivalents of hydroxyl residues in compound of formula (I).

Preferably, in REAC1 the diketene is charged to a mixture of polyol with BAS1.

Preferably, the reaction time of REAC1 is from 5 to 12 h, more preferably from 6 to 10 h, even more preferably from 6.5 to 8 h.

More preferably, the reaction time of REAC1 is devided into a time of charging, where the diketene is added to the mixture of polyol with BAS1, with this time of charging being from 5 to 8 h, preferably 5.5 to 8 h, and a time of stirring, wherein after the charging of the diketene the reaction mixture is stirred, with this time of stirring being from 0.25 to 4 h, preferably 0.25 to 2 h; with the time of charging and the time of stirring adding up to the reaction time.

In case of the polyol being a solid at ambient temperature, the reaction temperature of REAC1 is above the melting point of the polyol;

more preferably, the reaction is done at a temperature of from 30 to 120° C., more preferably of from 30 to 110° C., more preferably of from 35 to 105° C.

Especially, the charging during REAC1 is done at a temperature of from 30 to 120° C., more preferably of from 30 to 110° C., even more preferably of from 35 to 105° C.; and the stirring during REAC1 is done at a temperature of from 30 to 70° C., preferably of from 35 to 65° C.

Preferably, REAC1 is done under atmospheric pressure, REAC1 can also be done under a pressure above atmospheric pressure; for example when a reaction temperature is chosen that is above the boiling point of any of the components of reaction mixture.

After the reaction the acetoacetylated polyol can be isolated after REAC3 by standard means known to the skilled person, simple decharging from the reaction vessel.

EXAMPLES

Abbreviations

The following abbreviations are used:
AA content content of acetoacetoxy residue

Materials

The materials were used in the following qualities:

| | |
|---|---|
| diketene | >99.0% purity, Lonza Ltd, 3930 Visp, Switzerland |
| DABCO | 97% purity |
| DMAP | 99% purity |
| Polyols | purchased from commercial suppliers and were used as obtained. The quality ranged from 97 to 99.5% purity. |

Analytical Methods $^1$H NMR
Solvent: DMSO-d6
20 to 50 mg of sample were dissolved in 0.6 ml of DMSO-d6.
$^1$H(quantitative) NMR
Solvent: DMSO-d6
100 mg of benzoic acid and 200 mg of sample were dissolved in 3 ml of DMSO-d6.
$^{13}$C NMR
Solvent: DMSO-d6
20 to 50 mg of sample were dissolved in 0.6 ml of DMSO-d6.

Examples 1 to 6—Procedure for Liquid Polyols

Ethylene glycol (285.5 g, 4.600 mol) was charged into a 1.0 L reactor followed by the addition of DABCO (0.532 g, 4.600 mmol, 0.001 eq). The mixture was heated to 40° C. until DABCO was completely dissolved. Then diketene (765.7 g, 9.108 mol, 2 eq) was added over a time period of 7 h while the reaction temperature was maintained between 40 and 42° C. After completed dosage of diketene, the mixture was stirred for 30 min at 40° C., then 1038 g of a yellowish viscous product mixture was uncharged.

$^1$H- and $^{13}$C-NMR confirmed the formation of bis acetoacetoxylated ethylene glycol as the main product.

$^1$H(quantitative) NMR showed

| | |
|---|---|
| 84% | yield bis acetoacetoxylated ethylene glycol |
| 14% | yield mono acetoacetoxylated ethylene glycol |
| 69 wt % | acetoacetoxy group content, corresponding to |
| 94% | conversion based on diketene |

| Example | Substrate | Diketene eq | Yield [%] | AA content [wt %] | Diketene conversion [%] |
|---|---|---|---|---|---|
| 1 | Ethylene glycol | 2 | 84 | 69 | 94 |
| 2 | 1,2-Propanediol | 2 | n.d. | 65 | 94 |
| 3 | 2,3-Butanediol[a] | 2 | n.d.[b] | 60 | 91 |
| 4 | 1,4-Butanediol | 2 | 88 | 63 | 95 |
| 5 | 1,5-Pentanediol | 2 | 92 | 58 | 93 |
| 6 | Glycerol | 3 | 90 | 69 | 93 |
| 7 | Glycerol[c] | 3 | 92 | 69 | 94 |

[a]mixture of isomers.
[b]Not determinable due to signal overlap.
[c]0.001 eq DMAP instead of DABCO

Examples 8 to 15—Procedure for Solid Polyols

Isosorbide (487.0 g, 3.332 mol) was charged into a 1.0 L reactor followed by the addition of DABCO (0.380 g, 3.330 mmol, 0.001 eq). The mixture was heated to 70° C. until all solid was completely melted. Then diketene (560.2 g, 6.664 mol, 2 eq) was added over a time period of 6 h, while the reaction temperature was slowly decreased from 70 to 40° C. over the dosage time. After completed dosage, the mixture was stirred for 60 min at 40° C., then 1020 g of a brownish viscous product mixture was uncharged.

$^1$H NMR confirmed the formation of bis acetoacetoxylated isosorbide as the main product, accompanied by minor formation of mono acetoacetoxylated isosorbide.

$^1$H(quantitative) NMR showed

| | |
|---|---|
| 88% | yield bis acetoacetoxylated isosorbide |
| 48 wt % | acetoacetoxy group content corresponding to |
| 89% | conversion based on diketene. |

| Example | Substrate | Diketene eq | Temp. [° C.] | Yield [%] | AA content [wt %] | Diketene conversion [%] |
|---|---|---|---|---|---|---|
| 8 | Isosorbide | 2 | 70 | 88 | 48 | 89 |
| 9 | 1,6-Hexanediol | 2 | 50 | 91 | 56 | 95 |
| 10 | Tricyclo[5.2.1.0$^{2,6}$]decane-4,8-dimethanol[a] CAS 26896-48-0 | 2 | 70 | n.d.[b] | 46 | 93 |
| 11 | 1,4-Cyclohexanedimethanol[a] | 2 | 50 | n.d.[b] | 51 | 93 |
| 12 | 2,4-Butyne-1,4-diol | 2 | 70 | 87 | 63 | 93 |
| 13 | 2,5-Dimethyl-3-hexyne-2,5-diol | 2 | 100 | 85 | 49 | 90 |
| 14 | Trimethylolpropane | 3 | 70 | 87 | 63 | 95 |
| 15 | Sorbitol[c] | 6 | 100 | n.d.[b] | 67 | 91 |

[a] mixture of isomers.
[b] Not determinable due to signal overlap.
[c] 0.002 eq DABCO Examples 16 to 18—Procedure for Mixture of Polyols Sorbitol (200.4 g, 1.100 mol) and glycerol (50.0 g, 0.543 mol, 0.49 eq) were charged into a 1 L reactor followed by the addition of DABCO (0.254 g, 2.200 mmol, 0.002 eq). The mixture was heated to 100° C. Then diketene (765.7 g, 9.108 mol, 2 eq) was added to the suspension (Examples 16 and 18) or to the melt (Example 17) respectively, over a time period of 7 h, while the reaction temperature was maintained between 100 and 102° C. Then the mixture was stirred for 30 min at 60° C., then 889 g of a yellowish viscous product was uncharged.

| Example | Substrate 1 | Substrate 2 | AA content [wt %] | Diketene conversion [wt %] |
|---|---|---|---|---|
| 16 | Sorbitol | Glycerol (0.494 eq) | 68 | 91 |
| 17 | 2,3-Butanediol | 1,2-Propanediol (0.264 eq) | 62 | 92 |
| 18 | Glycerol | Pentaerythritol (0.182 eq) | 66 | 90 |

The invention claimed is:

1. A method for preparation of an acetoacetylated polyol, the method comprises a reaction REAC1, wherein a polyol is reacted with diketene;
REAC1 is done in the presence of a base BAS1;
BAS1 is DABCO or DMAP;
REAC1 is done in the absence of a solvent.

2. The method according to claim 1, wherein
only the three components polyol, BAS1 and diketene are used for and are charged for REAC1, and no other compounds are used for or are charged for or are present in REAL 1.

3. The method according to claim 1, wherein
the polyol is a compound of formula (I);

$$R1(OH)_{m1} \qquad (I)$$

R1 is selected from the group consisting of $C_{1-12}$ alkane, $C_{1-12}$ alkene, $C_{1-12}$ alkyne, $C_{5-12}$ cycloalkane, $C_{6-12}$ cycloalkene, $C_{8-12}$ di- and tricycloalkane, $C_{8-12}$ di- and tricycloalkene, and mixtures thereof;
wherein 1, 2 or 3 of any of the $CH_2$ group can be exchanged for O;
m1 is 2, 3, 4, 5 or 6.

4. The method according to claim 3, wherein
R1 is selected from the group consisting of $C_{1-12}$ alkane, $C_{1-12}$ alkene, Ci-12 alkyne, $C_{5-12}$ cycloalkane, $C_{8-12}$ di- and tricycloalkane, and mixtures thereof.

5. The method according to claim 1, wherein
the polyol is selected from the group consisting of di- and trimethylene glycol, ethylene glycol, di-, tri- and tetraethylene glycol, 1,2- and 1,3-propanediol, di- and tripropylene glycol, 1,2-, 1,3-, 1,4-, 2,3-, 2,4- and 3,4-butanediol, pentanediol, pentylglycol, neopentyl glycol, glycerol, isosorbide, hexanediol, hexylene glycol, trimethylpentanediol, tricyclo[5.2.1.0$^{2,6}$]decane-4,8-dimethanol, 1,2-, 1,3- and 1,4-cyclohexanedimethanol, 2,4-butyne-1,4-diol, 2,5-dimethyl-3-hexyne-2,5-diol, trimethylolethane, trimethylolpropane, sorbitol, pentaerythritol, and mixtures thereof.

6. The method according to claim 1, wherein
the polyol is selected from the group consisting of ethylene glycol, 1,4-butanediol, 1,5-pentanediol, 1,6-hexanediol, tricyclo[5.2.1.0$^{2,6}$]decane-4,8-dimethanol, 1,4-cyclohexanedimethanol and trimethylolpropane, and mixtures thereof.

7. The method according to claim 1, wherein
the polyol is selected from ethylene glycol and trimethylolpropane, and a mixture thereof.

8. The method according to claim 1, wherein
BAS1 is DABCO.

9. The method according to claim 1, wherein
in REAC1 the diketene is charged to a mixture of polyol with BAS1.

* * * * *